United States Patent [19]

DeRosch et al.

[11] Patent Number: 5,300,280
[45] Date of Patent: Apr. 5, 1994

[54] STABILIZED RADIOPHARMACEUTICAL KITS

[75] Inventors: Mark A. DeRosch, St. Louis; Edward A. Deutsch; Mary M. Dyszlewski, both of Maryland Heights; Dennis L. Nosco, Florissant, all of Mo.

[73] Assignee: Mallinckrodt Medical, Inc., St. Louis, Mo.

[21] Appl. No.: 836,644

[22] Filed: Feb. 14, 1992

[51] Int. Cl.$^5$ ............... A61K 43/00; A61K 49/02; A61K 31/715

[52] U.S. Cl. ................... 424/1.53; 424/1.11; 514/777; 514/778

[58] Field of Search .............. 536/103, 46; 514/58, 514/777, 778; 424/1.1

[56] References Cited

U.S. PATENT DOCUMENTS

| | | | |
|---|---|---|---|
| 4,714,605 | 12/1987 | Feld et al. | 424/1.1 |
| 4,727,064 | 2/1988 | Pitha | 514/58 |
| 4,764,604 | 8/1988 | Müller | 536/103 |
| 4,871,836 | 10/1989 | Francesconi et al. | 424/1.1 X |
| 4,917,879 | 4/1990 | Deutsch et al. | 424/1.1 |
| 5,024,998 | 6/1991 | Bodor | 424/1.1 X |
| 5,026,913 | 6/1991 | McBride et al. | 424/1.1 X |
| 5,068,227 | 11/1991 | Weinshenker | 424/1.1 X |
| 5,112,595 | 5/1992 | Woulfe et al. | 424/1.1 |

*Primary Examiner*—Robert L. Stoll
*Assistant Examiner*—John M. Covert
*Attorney, Agent, or Firm*—Brian K. Stierwalt; David A. Hey

[57] ABSTRACT

The present invention relates to the stabilization of radiopharmaceutical preparations and to the stabilization of components of radiopharmaceutical kits. In particular, the present invention relates to stabilization of lyophilized components of radiopharmaceutical kits by the addition of a cyclic oligosaccharide, such as, a modified or unmodified cyclodextrin, to the kit.

33 Claims, No Drawings

STABILIZED RADIOPHARMACEUTICAL KITS

BACKGROUND

The present invention relates to the stabilization of radiopharmaceutical preparations and to the stabilization of components of radiopharmaceutical kits. In particular, the present invention relates to stabilization of lyophilized components of radiopharmaceutical kits by the addition of a cyclic oligosaccharide, such as a modified or unmodified cyclodextrin, to the kit.

Modified cyclodextrins are known to be useful in stabilizing drugs. For example, U.S. Pat. No. 4,727,064 to Pitha describes pharmaceutical preparations consisting generally of a drug with a substantially low water-solubility and an amorphous, water-soluble complex of cyclodextrin. In particular, the Pitha patent describes (1) a method of converting drug compositions which are crystalline and of low water-solubility into intrinsically amorphous complexes which have improved pharmaceutical properties; and (2) the method comprising inclusion of multi-component mixtures of cyclodextrin derivatives in the drug compositions. Pitha points out that in order for the cyclodextrin derivatives to be effective in assisting dissolution of the drugs, that a substantial part of the drug molecule should fit into the hydrophobic cavity of the cyclodextrin molecule and the same part of the drug molecule should be hydrophobic. The method of Pitha is most directly concerned with stabilization of hormone compositions, such as testosterone, progesterone, and estrogenic drugs.

European Patent 149,197 to Brauns et al, also relates to ways of increasing the solubility of drug compositions which are sparingly water-soluble by themselves. Brauns et al particularly relates to pharmaceutical preparations containing such drug compositions and a partially etherified beta-cyclodextrin. Brauns et al also indicates that medicinal substances which exhibit the greatest increased water-solubility when converted to inclusion complexes with the beta-cyclodextrin are those having a corresponding fitting shape, i.e. they have to fit into the cavity of the beta-cyclodextrin cyclic system. Examples of such medicinal substances mentioned in Brauns et al, include non-steroidal antirheumatic agents, steroids, cardiac glycosides and derivatives of benzodiazepin; benzimidazole, piperidine, piperizine, imidazole, and triazole.

However, the prior art does not relate to stabilization of radiopharmaceutical preparations or to kits for forming radiopharmaceuticals. Further, the prior art relates only to formation of inclusion complexes wherein the drug fits within the framework of the modified cyclodextrin. Finally, the prior art does not relate to the stabilization of volatile components of a radiopharmaceutical kit.

Therefore, there remains a need to develop stabilization techniques for radiopharmaceutical kits.

OBJECTS OF THE INVENTION

It is one object of the present invention to provide means of stabilizing volatile and/or oxidizable components of radiopharmaceutical preparations.

It is another object of the present invention to provide means of stabilizing the components of radiopharmaceutical kits.

SUMMARY OF THE INVENTION

These objects and others as will be apparent from the following discussion are accomplished according to the present invention by the addition of stabilizing amounts of a cyclic oligosaccharide, such as a modified or unmodified cyclodextrin, to the radiopharmaceutical kit.

DETAILED DESCRIPTION OF THE INVENTION

Kits of the type used to make radiopharmaceuticals containing radioactive metals (e.g. Tc-99m, Re-186, and Re-188) normally include at least one ligand capable of bonding to the radioactive metal, a reducing agent, an inert, pharmaceutically acceptable carrier and auxiliary substances such as anti-oxidants, stabilizers and bulking agents, all combined and stored in a lyophilized condition. To form the radiopharmaceutical composition, the ingredients of the kit are combined with a radioactive ingredient such as technetium or rhenium in the form of a radioactive solution.

Components of the radiopharmaceutical kit are sometimes volatile or oxidizable thereby requiring storage under refrigerated and air-tight conditions. Volatilization can occur during the lyophilization process, or during storage, with subsequent deleterious leakage from the storage container, oxidation or adsorption to the storage vial or vial stopper. Oxidation may occur by interaction with molecular oxygen, sterilizing radiation, or other components of the kit.

In particular, radiopharmaceutical kits normally include at least one lyophilized ligand which is capable of bonding to a radioisotope during formulation to produce a radiopharmaceutical solution. These ligands are sometimes very susceptible to volatilization and/or oxidation.

Ligands that may be used in radiopharmaceutical kits include phosphines, arsines, thiols, thioethers, isonitriles, amines and ligands including combinations of these groups. Such ligands are susceptible to volatilization and/or oxidation because they comprise organic compounds that are generally oxygen sensitive or which, under normal circumstances, are unable to be lyophilized because they are liquids or sublimable solids. Particular ligands which have shown a relatively high risk of volatilization and/or oxidation are those ligands which include 1 to 4 phosphine groups per molecule.

Particular examples of ligands which may be components of a radiopharmaceutical kit are phosphine ligands such as: tris(3-ethoxypropyl)phosphine (TEPP); trimethylphosphine ($PMe_3$); triethylphosphine ($PEt_3$); tris(3-methoxy-3-methylbutyl)phosphine; tris(3-methoxypropyl)phosphine (TMPP); tris[2-[2-(1,3-dioxanyl)]]ethylphosphine; tris[2-[2-(1,3-dioxolanyl)]]ethylphosphine; methylbis(3-methoxypropyl)phosphine; tris(4-methoxybutyl)phosphine (TMBP); dimethyl(3-methoxypropyl)phosphine; methylbis[2-[2-(1,3-dioxanyl)]]ethylphosphine; bis(1,2-dimethylphosphino)ethane (DMPE); 1,3-bis(dimethylphosphino)-2,2-di(methoxymethyl)propane; or 1,2-bis(di((2-ethoxy)ethyl)phosphino)ethane.

It has been discovered that cyclic oligosaccharides act as effective stabilizers for radiopharmaceutical kits. In particular, modified or unmodified cyclodextrins have been found to provide superior stabilization qualities. From preliminary studies, it is believed that the addition of cyclic oligosaccharides, such as modified or unmodified cyclodextrin, to the radiopharmaceutical kits helps to inhibit oxidation of the kit components and to inhibit the volatilization of generally non-lyophilizable components. However, other mechanisms of stabilization can not be entirely ruled out at this time.

Because modified or unmodified cyclodextrins have a hydrophobic interior, their use is especially attractive for stabilization of the organic ligands included in a radiopharmaceutical kit. The addition of modified or unmodified cyclodextrins to a kit formulation which includes such organic compounds acts to inhibit the disadvantageous oxidation and/or volatilization.

The modified or unmodified cyclodextrin must be pharmaceutically acceptable and may be selected from α-cyclodextrins, β-cyclodextrins, γ-cyclodextrins, and combinations thereof. Particular α-cyclodextrins which may be used in the kits according to the present invention are hydroxypropyl-α-cyclodextrin, and hydroxyethyl-α-cyclodextrin.

Particular β-cyclodextrins which may be used in the kits according to the present invention are hydroxypropyl-β-cyclodextrin, carboxymethyl-β-cyclodextrin, dihydroxypropyl-β-cyclodextrin, hydroxyethyl-β-cyclodextrin, 2,6-di-O-methyl-β-cyclodextrin, and sulfated-β-cyclodextrin. Preferably, hydroxypropyl-α-cyclodextrin is added to the kits according to the present invention.

Particular γ-cyclodextrins which may be used in the kits according to the present invention are hydroxypropyl-γ-cyclodextrin, dihydroxypropyl-γ-cyclodextrin, hydroxyethyl-γ-cyclodextrin, and sulfated-γ-cyclodextrin.

The cyclic oligosaccharide should be included in an amount suitable to inhibit oxidation and/or volatilization of the kit components. Preferably, when the cyclic oligosaccharide is a modified or unmodified cyclodextrin, it is included in an amount of 10 to 100 mg. More preferably, the modified or unmodified cyclodextrin is included in an amount of 25 to 50 mg.

The addition of modified or unmodified cyclodextrin to a radiopharmaceutical kit has also been found to provide further advantages. In particular, modified or unmodified cyclodextrins aid in the solubilization of other kit components, especially during preparation of the bulk solutions that are dispensed prior to lyophilization. Moreover, modified or unmodified cyclodextrins act as good bulking agents for the kit.

Radiopharmaceutical kits to which cyclic oligosaccharides such as modified or unmodified cyclodextrins have been added have been found to exhibit good stabilization characteristics, with subsequent improved performance over non-stabilized kits. In particular, the presence of modified or unmodified cyclodextrin in the kit acts to enhance the shelf life of the kit.

A radiochemical purity test was carried out to analyze the stabilization effect of cyclic oligosaccharides in radiopharmaceutical kits. In particular, a kit useful for making myocardial imaging agents and containing a first ligand capable of bonding to a radioisotope and a phosphine ligand also capable of bonding to the radioisotope, i.e. tris(3-methoxypropyl)phosphine (TMPP), was studied. The radiochemical purity of kits containing modified cyclodextrins were compared to the radiochemical purity of kits with no added cyclodextrin. All of the kits tested were prepared and stored under like conditions for comparison purposes. The collected data is shown below in TABLE 1, which shows that the addition of cyclodextrin increases shelf life more than 100-fold.

TABLE 1

| KIT | INITIAL | 1 WEEK | | 2 WEEKS | | 3 MONTHS | |
| --- | --- | --- | --- | --- | --- | --- | --- |
| | | RT | 50° C. | RT | 50° C. | RT | 50° C. |
| No CD | 98.0% | 97.1% | 36.6% | 97.3% | 8.3% | 0% | 0% |
| α-CD | 92.5% | 92.4% | 91.4% | 90.9% | 89.4% | 90.9% | — |
| HPβ-CD | 92.2% | 95.6% | 95.7% | 95.0% | 95.5% | 94.3% | 94.8% |
| γ-CD | 92.5% | 93.9% | 89.8% | 92.4% | 90.0% | 95.2% | — |

The kits studied in TABLE 1, contained the following components:
  20 mg of a ligand capable of bonding to a radioisotope
  1.5 mg tris(3-methoxypropyl)phosphine (TMPP) ligand
  1.5 mg sodium carbonate
  2.0 mg sodium ascorbate
  0.24 mg of copper salt
  50 mg of α-, HPβ-, γ-, or no cyclodextrin (CD).

The kits were placed in storage at both 50° C. and room temperature (RT) after initial testing.

As can be seen from TABLE 1, all of the kits, even those without cyclodextrin, remain stable at room temperature for at least two weeks. From preliminary analysis of the analytical data, it is believed that the drop in radiochemical purity is caused by volatilization and/or oxidation of the TMPP in the kits. Radiochemical Purity HPLC studies indicated that all three cyclodextrins appear to stabilize the lyophilized kit both at room temperature and 50° C. storage. These data suggest that the cyclodextrins act to inhibit the volatilization and/or oxidation of TMPP since there is no appreciable drop in radiochemical purity. Finally as can be seen from TABLE 1, the derivatized HPβ-cyclodextrin yielded the best results.

The following Examples relate to general synthetic methods of forming lyophilized kits according to the present invention.

EXAMPLE 1

General procedure for the dispensing and lyophilization of cold kits for the preparation of a technetium-99m(III) myocardial imaging agent.

Add 300 g of a modified or unmodified cyclodextrin and 120 g of Schiff base ligand to approximately 7 L of purged water for injection and stir until dissolved. Add and dissolve 12.0 g of sodium ascorbate followed by 9.0 g of sodium carbonate. Next, weigh 9.0 g phosphine ligand into 500 mL of argon purged WFI and shake to dissolve phosphine. Under argon flow, add 1.4 g of copper salt to aqueous phosphine and shake until dissolution is complete. Then, add Cu(I)/phosphine solution to bulk solution. With all the materials in solution, bring volume to 12.0 L, and subsequently sterilize the final solution by filtration using a 0.2 μ filter. Dispense 2.0 mL aliquots into 6000 dry, sterile, pyrogen-free, 6 mL glass tubing vials and insert lyophilization stoppers (siliconized) to the upper position for lyophilization. Next, place the vials in a pre-cooled shelf of the lyophilizer and lyophilize to a product moisture level of mg of water. Finally, following lyophilization, back-fill chamber with argon gas and insert stoppers to fully closed position. Remove vials and apply crimp caps.

Recommended starting lyophilization conditions include:

a. Freeze product vials on the shelf to a temperature of −35° C. or colder.
b. Apply vacuum when product temperature is <−35° C. and condenser temperature is −50° C. or colder.
c. After chamber pressure reaches 60 microns or less, apply shelf heat to −30° C.
d. Hold shelf temperature at −30° C. until product thermocouples reach or go above −30° C. Then ramp up shelf heat at a rate of 6° C./hour until the product temperature reaches approximately +35° C. for a minimum of 6 hours.

EXAMPLE 2

General procedure for the labeling and QC of a lyophilized cold kit for the preparation of a technetium-99m(III) myocardial imaging agent.

To prepare technetium-99m complex, add two milliliters of sodium pertechnetate Tc-99m injection to a freeze-dried kit and swirl the contents of the vial for a few seconds. Immediately following reconstitution, place vials upright in a boiling water bath for 15 minutes. After boiling, allow vials to cool to room temperature which yields a technetium-99m complex ready for use. The radiochemical purity is determined by HPLC on a PRP-1 (250×4.1 mm, 10 μ) column using an acetonitrile:$KH_2PO_4$ gradient mobile phase at 2.0 mL/min. Typical radiochemical purities are 92–96%.

The foregoing has been a description of certain preferred embodiments of the present invention, but is not intended to limit the invention in any way. Rather, many modifications, variations and changes in details may be made within the scope of the present invention.

What is claimed is:

1. A method of stabilizing components of a radiopharmaceutical kit, said method comprising:
   including in said kit at least one ligand capable of bonding to a radioisotope during radiopharmaceutical solution formulation;
   wherein said ligand is selected from the group consisting of phosphines, arsines, thiols, thioethers, and isonitriles; and
   including in said kit, a cyclic oligosaccharide in an amount suitable to inhibit oxidation and/or volatilization of said components.

2. A method according to claim 1, wherein said ligand is a phosphine ligand having 1 to 4 phosphine groups per molecule.

3. A method according to claim 1, wherein said ligand is a phosphine ligand selected from the group consisting of
tris(3-ethoxypropyl)phosphine (TEPP);
trimethylphosphine ($PMe_3$);
triethylphosphine ($PEt_3$);
tris(3-methoxy-3-methylbutyl)phosphine;
tris(3-methoxypropyl)phosphine (TMPP);
tris[2-[2-(1,3-dioxanyl)]]ethylphosphine;
tris[2-[2-(1,3-dioxolanyl)]]ethylphosphine;
methylbis(3-methoxypropyl)phosphine;
tris(4-methoxybutyl)phosphine (TMBP);
dimethyl(3-methoxypropyl)phosphine;
methylbis[2-[2-(1,3-dioxanyl)]]ethylphosphine;
bis(1,2-dimethylphosphino)ethane (DMPE);
1,3-bis(dimethylphosphino)-2,2-di(methoxymethyl)propane; or
1,2-bis(di((2-ethoxy)ethyl)phosphino)ethane.

4. A method according to claim 3, wherein said phosphine ligand is
bis(1,2-dimethylphosphino)ethane (DMPE);
1,3-bis(dimethylphosphino)-2,2-di(methoxymethyl)propane; or
1,2-bis(di((2-ethoxy)ethyl)phosphino)ethane.

5. A method according to claim 3, wherein said phosphine ligand is
tris(3-methoxypropyl)phosphine (TMPP).

6. A method according to claim 1, wherein said cyclic oligosaccharide is a modified or unmodified cyclodextrin.

7. A method according to claim 6, wherein said modified or unmodified cyclodextrin is selected from the group consisting of α-cyclodextrin, β-cyclodextrin, and γ-cyclodextrin.

8. A method according to claim 7, wherein said modified or unmodified cyclodextrin is an α-cyclodextrin selected from the group consisting of hydroxypropyl-α-cyclodextrin, and hydroxyethyl-α-cyclodextrin.

9. A method according to claim 7, wherein said modified or unmodified cyclodextrin is a β-cyclodextrin selected from the group consisting of hydroxypropyl-β-cyclodextrin, carboxymethyl-β-cyclodextrin, dihydroxypropyl-β-cyclodextrin, hydroxyethyl-β-cyclodextrin, 2,6-di-O-methyl-β-cyclodextrin, and sulfated-β-cyclodextrin.

10. A method according to claim 9, wherein said β-cyclodextrin is hydroxypropyl-β-cyclodextrin.

11. A method according to claim 7, wherein said modified or unmodified cyclodextrin is a γ-cyclodextrin selected from the group consisting of hydroxypropyl-γ-cyclodextrin, dihydroxypropyl-γ-cyclodextrin, hydroxyethyl-γ-cyclodextrin, and sulfated-γ-cyclodextrin.

12. A method according to claim 6, wherein said modified or unmodified cyclodextrin is included in said kit in an amount of 10 to 100 mg.

13. A method according to claim 12, wherein said modified or unmodified cyclodextrin is included in said kit in an amount of 25 to 50 mg.

14. A method according to claim 11, wherein said radioisotope is technetium or rhenium.

15. A method according to claim 14, wherein said radioisotope is technetium-99m, rhenium-186, or rhenium-188.

16. A method of enhancing shelf life of a radiopharmaceutical kit, said method comprising:
   including a cyclic oligosaccharide in said kit;
   wherein said kit comprises at least one ligand capable of bonding to a radioisotope during radiopharmaceutical solution formation, and
   wherein said ligand is selected from the group consisting of phosphines, arsines, thiols, thioethers, and isonitriles.

17. A method according to claim 16, wherein said ligand is a phosphine ligand having 1 to 4 phosphine groups per molecule.

18. A method according to claim 16, wherein said ligand is a phosphine ligand selected from the group consisting of
tris(3-ethoxypropyl)phosphine (TEPP);
trimethylphosphine ($PMe_3$);
triethylphosphine ($PEt_3$);
tris(3-methoxy-3-methylbutyl)phosphine;

tris(3-methoxypropyl)phosphine (TMPP);
tris[2-[2-(1,3-dioxanyl)]]ethylphosphine;
tris[2-[2-(1,3-dioxolanyl)]]ethylphosphine;
methylbis(3-methoxypropyl)phosphine;
tris(4-methoxybutyl)phosphine (TMBP);
dimethyl (3-methoxypropyl)phosphine;
methylbis[2-[2-(1,3-dioxanyl)]]ethylphosphine;
bis(1,2-dimethylphosphino)ethane (DMPE);
1,3-bis(dimethylphosphino)-2,2-di(methoxymethyl)propane; or
1,2-bis(di((2-ethoxy)ethyl)phosphino)ethane.

19. A method according to claim 18, wherein said phosphine ligand is
bis(1,2-dimethylphosphino)ethane (DMPE);
1,3-bis(dimethylphosphino)-2,2-di(methoxymethyl)propane; or
1,2-bis(di((2-ethoxy)ethyl)phosphino)ethane.

20. A method according to claim 18, wherein said phosphine ligand is
tris(3-methoxypropyl)phosphine (TMPP).

21. A method according to claim 16, wherein said cyclic oligosaccharide is a modified or unmodified cyclodextrin.

22. A method according to claim 21, wherein said modified or unmodified cyclodextrin is selected from the group consisting of α-cyclodextrin, β-cyclodextrin, and γ-cyclodextrin.

23. A method according to claim 22, wherein said modified or unmodified cyclodextrin is an α-cyclodextrin selected from the group consisting of hydroxypropyl-α-cyclodextrin, and hydroxyethyl-α-cyclodextrin.

24. A method according to claim 22, wherein said modified or unmodified cyclodextrin is a β-cyclodextrin selected from the group consisting of hydroxypropyl-≠2-cyclodextrin, carboxymethyl-β-cyclodextrin, dihydroxypropyl-β-cyclodextrin, hydroxyethyl-β-cyclodextrin, 2,6-di-O-methyl-β-cyclodextrin, and sulfated-β-cyclodextrin.

25. A method according to claim 24, wherein said β-cyclodextrin is hydroxypropyl-β-cyclodextrin.

26. A method according to claim 22, wherein said modified or unmodified cyclodextrin is a γ-cyclodextrin selected from the group consisting of hydroxypropyl-γ-cyclodextrin, dihydroxypropyl-γ-cyclodextrin, hydroxyethyl-γ-cyclodextrin, and sulfated-γ-cyclodextrin.

27. A method according to claim 21, wherein said modified or unmodified cyclodextrin is included in said kit in an amount of 10 to 100 mg.

28. A method according to claim 27, wherein said modified or unmodified cyclodextrin is included in said kit in an amount of 25 to 50 mg.

29. A method according to claim 16, wherein said radioisotope is technetium or rhenium.

30. A method according to claim 29, wherein said radioisotope is technetium-99m, rhenium-186, or rhenium-188.

31. A method according to claim 16, wherein said cyclic oligosaccharide is included in said kit in an amount suitable to inhibit oxidation and/or volatilization of said ligand.

32. A kit for making radiopharmaceuticals containing radioactive metals, said kit comprising
a ligand capable of bonding to a radioisotope during radiopharmaceutical solution formulation,
tris(3-methoxypropyl)phosphine (TMPP) ligand,
sodium carbonate,
sodium ascorbate,
a copper salt, and
a cyclic oligosaccharide as a stabilizing compound.

33. A kit according to claim 32, wherein said kit is used for preparation of a technetium-99m(III) myocardial imaging agent, further wherein said cyclic oligosaccharide is a cyclodextrin selected from the group consisting of α-cyclodextrins, β-cyclodextrins, and γ-cyclodextrins, and wherein said kit components are present in the following amounts,
20 mg of said ligand,
1.5 mg of said tris(3-methoxypropyl)phosphine (TMPP) ligand,
1.5 mg of said sodium carbonate,
2.0 mg of said sodium ascorbate,
0.24 mg of said copper salt, and
50 mg of said cyclic oligosaccharide.

* * * * *